United States Patent [19]
Sakata et al.

[11] Patent Number: 4,525,457
[45] Date of Patent: Jun. 25, 1985

[54] METHOD OF IMMOBILIZING ENZYMATICALLY ACTIVE MATERIALS

[75] Inventors: Ko Sakata, Kawasaki; Hirosuke Imai, Yokohama, both of Japan

[73] Assignee: Nippon Oil Co., Ltd., Tokyo, Japan

[21] Appl. No.: 487,574

[22] Filed: Apr. 22, 1983

[30] Foreign Application Priority Data

Apr. 27, 1982 [JP] Japan ................... 57-69510

[51] Int. Cl.$^3$ ...................... C12N 11/10; C12N 11/08
[52] U.S. Cl. .................................... 435/178; 435/179; 435/180; 435/181
[58] Field of Search ................................ 435/180, 181

[56] References Cited

U.S. PATENT DOCUMENTS 4,194,066  3/1980  Kaetsu et al. ....................... 435/182

*Primary Examiner*—Sam Rosen
*Attorney, Agent, or Firm*—Fisher, Christen & Sabol

[57] ABSTRACT

This invention discloses a method of immobilizing an enzymatically active material to a water-insoluble polyanion which comprises bringing a polycation-containing aqueous medium and the enzymatically active substance into contact with the water-insoluble polyanion having any desired form. This method is characterized in that the enzymatically active substance is adsorbed on the surfaces of the water-insoluble polyanion and, at the same time, a strong complex is formed by the interaction of the polycation and the polyanion to produce a water-insoluble film. As a result, the enzymatically active substance so adsorbed is securely fixed to the surfaces of the water-insoluble polyanion and scarcely released therefrom.

6 Claims, No Drawings

METHOD OF IMMOBILIZING ENZYMATICALLY ACTIVE MATERIALS

BACKGROUND OF THE INVENTION

1. Field of the Invention

This invention relates to a novel method of immobilizing enzymatically active materials and, more particularly, to a method of immobilizing an enzymatically active material to a water-insoluble polyanion which comprises bringing a polycation-containing aqueous medium and the enzymatically active material into contact with the water-insoluble polyanion.

2. Description of the Prior Art

Conventionally, a number of techniques for immobilizing enzymatically active materials are well known which include, for example, the method of chemically combining an enzymatically active material with another enzymatically active material or an insoluble carrier by covalent or ionic bonding and the method of entrapping an enzymatically active material within a water-insoluble substance or microcapsules. Among the rest, the adsorption method in which an enzymatically active material is fixed on the surfaces of an inert carrier by ionic or other physical force has several advantages over other immobilization methods. For example, the adsorption method permits an enzymatically active material to be immobilized under very mild conditions and bound loosely to a carrier. Thus, the enzymatically active material suffers little damage from the immobilization procedure and, after being once immobilized, it undergoes only a slight degree of deactivation. Moreover, the adsorption method permits the enzymatically active material to be fixed in the vicinity of the surfaces of the carrier. Accordingly, when a substrate is brought into contact with the immobilized preparation of the enzymatically active material, the substrate readily spreads over the enzymatically active material, so that it can exhibit high activity even in the immobilized state. Furthermore, it is possible to prepare and pretreat the carrier in the absence of enzymatically active material. Thus, as compared with the preparation and pretreatment of a carrier in other immobilization methods, greater latitude is given in determining the type of carrier used and the method of preparation. This makes it possible to select a carrier highly suitable for the intended purpose. A further advantage of the adsorption method is that the immobilization procedure can be carried out in a culture vessel or the like. This serves not only to largely decrease the risk of contamination with undesired microorganisms during the procedure for immobilizing an enzymatically active material, but also to simplify the immobilization procedure to a remarkable degree.

With all these advantages, the adsorption method still has many disadvantages and cannot be regarded as a satisfactory method of immobilizing enzymatically active materials. Specifically, as compared with the above-described chemical and physical immobilization methods, the adsorption method is disadvantageous in that the immobilization procedure has low efficiency and requires a long period of time. Moreover, since the adsorption depends largely on the surface condition of the carrier the enzymatically active material is liable to desorption due to the change in the surface conditions of the carrier during use. Furthermore, the adsorptive power of the enzymatically active material to the carrier is so low that, during the immobilization of the enzymatically active material or during the use of the resulting immobilized preparation, the enzymatically active material tends to be released from the carrier under the influence of mechanical shock and the like. In addition, when living microbial cells and the like are used as the enzymatically active material, most of the newly grown cells are released from the carrier. This makes the adsorption method unsuitable for the immobilization of growing microbial cells.

SUMMARY OF THE INVENTION

It is an object of the present invention to provide a novel method of enzymatically active materials which comprises bringing a polycation-containing aqueous medium and an enzymatically active material into contact with a water-insoluble polyanion.

According to the method of the present invention, a polycation-containing aqueous medium and an enzymatically active material are brought into contact with a water-insoluble polyanion having any desired form, whereby the enzymatically active material is immobilized, simultaneously with the formation of a film, in the vicinity of the surface of the water-insoluble polyanion.

DETAILED DESCRIPTION OF THE PREFERRED EMBODIMENTS

When compared with the prior art adsorption method, the method of the present invention has the following advantages:

(a) The rate of adsorption of an enzymatically active material is markedly increased.

(b) An immobilized preparation can be obtained in high yield and with good reproducibility.

(c) Once an enzymatically active material is immobilized, it is scarcely released.

(d) Where living microbial cells are immobilized, newly grown microbial cells are also immobilized.

(e) An enzymatically active material can be immobilized without regard to the surface condition of the water-insoluble polyanion.

(f) The life of the enzyme activity is prolonged.

(g) This method is unlimitedly applicable to a wide variety of enzymatically active materials.

(h) Little damage is caused to the enzymatically active material.

In addition, the method of the present invention also has the advantages possessed by the prior art adsorption method. Specifically, the method of the present invention is also characterized, for example, good contact between the substrate and the enzymatically active material, simplicity of operation, little risk of contamination with undesired microorganisms, and the like.

Furthermore, when compared with the prior art covalent bonding method, the method of the present invention is characterized by less damage to the enzymatically active material and more simplicity of operation. When compared with the prior art entrapping method, the method of the present invention is characterized by less release of the enzymatically active material, a longer life of the enzyme activity, less risk of contamination with undesired microorganisms during the immobilization procedure.

No particular limitation is placed on the type of polycation used in the present invention, provided that it can react with a polyanion as described hereinbelow to form a complex. The polycations which can be used in the present invention are exemplified by the following polymers.

(I) Polymers containing a quaternary ammonium ion group in the backbone

Typical examples of such polymers are:

(a) Homopolymers, copolymers and graft polymers having structural units of the general formula $$-\underset{\underset{R_4\ x^{\ominus}}{|}}{\overset{\overset{R_1}{|}}{CH}}-\underset{}{\overset{\overset{R_2}{|}}{CH}}-\overset{\overset{R_3}{|}}{\overset{\oplus}{N}}-$$

where $R_1$ and $R_2$ are hydrogen atoms or alkyl radicals having not more than 4 carbon atoms, and $R_3$ and $R_4$ are alkyl radicals having not more than 4 carbon atoms;

(b) Homopolymers, copolymers and graft polymers having structural units of the general formula $$-(-CH_2-)_m\overset{\overset{R_1}{|}}{\underset{\underset{R_3\ x^{\ominus}}{|}}{\overset{\oplus}{N}}}-\overset{R_2}{|}-$$

where $R_1$ is a hydrogen atom or an alkyl radical having not more than 4 carbon atoms, $R_2$ and $R_3$ are alkyl radicals having not more than 4 carbon atoms, and m is a whole number of 3 or more; and (c) Homopolymers, copolymers and graft polymers having structural units of the general formula

[cyclic ammonium structure with CH, CH2 groups, N⊕, R1, R2, x⊖]

where $R_1$ and $R_2$ are alkyl radicals having not more than 4 carbon atoms or allyl radicals.

(II) Polymers containing a quaternary ammonium salt group in the side chains

Typical examples of such polymers are:

(a) Homopolymers, copolymers and graft polymers having structural units of the general formula $$-CH_2-\underset{\underset{\overset{\|}{O}}{C}}{\overset{\overset{R_1}{|}}{C}}-\;\;\;\overset{R_2}{\underset{}{|}}\;\;\overset{R_3}{\underset{}{|}}\;\;\;\;\overset{R_4}{\underset{}{|}}$$
$$C(-O-CH-CH-)_m(-CH_2-)_n\overset{\oplus}{N}-R_5\ x^{\ominus}$$
$$\overset{}{\underset{R_6}{|}}$$

where $R_1$, $R_2$ and $R_3$ are hydrogen atoms or methyl radicals, $R_4$ and $R_5$ are alkyl radicals having not more than 4 carbon atoms, $R_6$ is an alkyl radical having not more than 4 carbon atoms, a benzyl radical, an allyl radical, an alkoxyl radical or a carbonamide group, m is a whole number of 1 to 30, and n is a whole number of 0 to 5;

(b) Homopolymers, copolymers and graft polymers having structural units of the general formula $$-CH_2-\overset{\overset{R_1}{|}}{\underset{\underset{\overset{\|}{O}}{C}}{C}}-\;\;\;\overset{R_2}{\underset{}{|}}\;\;\overset{R_3}{\underset{}{|}}\;\;\;\;\overset{R_5}{\underset{}{|}}$$
$$C(-O-CH-CH-CH-)_n\overset{\oplus}{N}-R_6\ x^{\ominus}.$$
$$\overset{}{\underset{R_7}{|}}$$

where $R_1$ is a hydrogen atom or a methyl radical, $R_2$, $R_3$ and $R_4$ are hydrogen atoms, methyl radicals or hydroxyl groups, $R_5$ and $R_6$ are alkyl radicals having not more than 4 carbon atoms, $R_7$ is an alkyl radical having not more than 4 carbon atoms, an allyl radical or an alkoxyl radical, and n is a whole number of 1 to 4;

(c) Homopolymers, copolymers and graft polymers having structural units of the general formula $$-CH_2-\overset{\overset{R_1}{|}}{C}-$$
$$\overset{|}{C}=O$$
$$\overset{|}{N}(-CH_2-)_n\overset{\overset{R_2}{|}}{\underset{\underset{R_4}{|}}{\overset{\oplus}{N}}}-R_3\ x^{\ominus}$$
$$\overset{|}{H}$$

where $R_1$ is a hydrogen atom or a methyl radical, $R_2$ and $R_3$ are alkyl radicals having not more than 4 carbon atoms, $R_4$ is an alkyl radical having not more than 4 carbon atoms or a benzyl radical, and n is a whole number of 1 to 4;

(d) Homopolymers, copolymers and graft polymers having structural units of the general formula $$-CH_2-\overset{\overset{R_1}{|}}{C}-$$
[phenylene ring]
$$CH_2-\overset{\overset{R_2}{|}}{\underset{\underset{R_4}{|}}{\overset{\oplus}{N}}}-R_3\ x^{\ominus}$$

where $R_1$ is a hydrogen atom or a methyl radical, and $R_2$, $R_3$ and $R_4$ are alkyl radicals having not more than 4 carbon atoms;

(e) Homopolymers, copolymers and graft polymers having structural units of the general formula

[pyridinium-type ring structures with substituents R, R1, R2, R3, R4 and counterion x⊖]

where $R_1$, $R_2$, $R_3$ and $R_4$ are hydrogen atoms or methyl radicals, and R is an alkyl radical having not more than 5 carbon atoms; and the like.

(III) Polymers containing an amine group or a salt thereof in the backbone

Typical examples of such polymers are:
(a) Homopolymers, copolymers and graft polymers having structural units of the general formula $$-\underset{\underset{H}{|}}{C}H-\underset{\underset{H}{|}}{C}H-\underset{\underset{R_3}{|}}{N}-$$

or a salt thereof, where $R_1$, $R_2$ and $R_3$ are hydrogen atoms or alkyl radicals having not more than 4 carbon atoms;

(b) Homopolymers, copolymers and graft polymers having structural units of the general formula

[piperidine ring structure with ethyl substituent, N–R]

or a salt thereof, where R is an alkyl radical having not more than 4 carbon atoms; and the like.

(IV) Polymers containing an amine group or a salt thereof in the side chains

Typical examples of such polymers are:
(a) Homopolymers, copolymers and graft polymers having structural units of the general formula $$-CH_2-\underset{\underset{R_2-N-R_3}{|}}{\overset{\overset{R_1}{|}}{C}}-$$

or a salt thereof, where $R_1$ is a hydrogen atom or a methyl radical, and $R_2$ and $R_3$ are hydrogen atoms or alkyl radicals having not more than 4 carbon atoms;

(b) Homopolymers, copolymers and graft polymers having structural units of the general formula $$-CH_2-\underset{\underset{\underset{O}{\|}}{C+O-CH-CH\underset{m}{)}+CH_2\underset{n}{)}N\underset{R_5}{\overset{R_4}{<}}}}{\overset{\overset{R_1}{|}}{C}}-$$
$\phantom{xxxxxx}$ $R_2$ $\phantom{x}$ $R_3$ or a salt thereof, where $R_1$, $R_2$ and $R_3$ are hydrogen atoms or methyl radicals, $R_4$ and $R_5$ are hydrogen atoms, alkyl radicals having not more than 4 carbon atoms, benzyl radicals, allyl radicals or alkoxyl radicals, m is a whole number of 1 to 30, and n is a whole number of 0 to 35;

(c) Homopolymers, copolymers and graft polymers having structural units of the general formula $$-CH_2-\underset{\underset{\underset{NH+CH_2\underset{n}{)}N\underset{R_3}{\overset{R_2}{<}}}{|}}{\underset{C=O}{|}}}{\overset{\overset{R_1}{|}}{C}}-$$

or a salt thereof, where $R_1$ is a hydrogen atom or a methyl radical, $R_2$ and $R_3$ are hydrogen atoms, alkyl radicals having not more than 4 carbon atoms, benzyl radicals or alkoxyl radicals;

(d) Homopolymers, copolymers and graft polymers having structural units of the general formula $$-CH_2-\underset{\underset{\underset{CH_2-N\underset{R_3}{\overset{R_2}{<}}}{|}}{\underset{[phenyl]}{|}}}{\overset{\overset{R_1}{|}}{C}}-$$

or a salt thereof, where $R_1$ is a hydrogen atom or a methyl radical, and $R_2$ and $R_3$ are hydrogen atoms or alkyl radicals having not more than 4 carbon atoms;

(e) Homopolymers, copolymers and graft polymers having structural units of the general formula

[pyridine-substituted vinyl structures with substituents $R_1$, $R_2$, $R_3$, $R_4$]

or a salt thereof, where $R_1$, $R_2$, $R_3$ and $R_4$ are hydrogen atoms or methyl radicals;

(f) Amino sugars (such as chitosan) and salts thereof; and the like.

In the practice of the present invention, polymers falling under any one of the above categories I to IV may be used, either alone or in admixture, as the polycation. It is also possible to use polymers falling under two or more of the above categories I to IV.

In the above categories I and II, $x^{\ominus}$ is an atom or atomic group constituting an anion. Where $x^{\ominus}$ is a monovalent anion, typical examples thereof include halogen anions, nitrate anion, nirite anion, sulfuric monoester anions (such as monomethyl sulfate and monoethyl sulfate anions), cyanide anion, formate anion, acetate anion, propionate anion and the like. On the other hand, where $x^{\ominus}$ is a divalent, typical examples thereof include sulfate anion, carbonate anion, thiosulfate anion and the like. In the case of a divalent anion, it is used in an amount equal to one-half that of a monovalent anion.

In the above categories III and IV, a salt of an amine group is a salt formed by the reaction of a group derived from a primary, secondary or tertiary amine with an acidic substance. Typically, inorganic acids such as hydrochloric acid, sulfuric acid, nitric acid, etc. and organic acids such as formic acid, acetic acid, propionic acid, etc. are used as the acidic substance.

In the polycation used in the present invention, the cationic structural units containing a quaternary ammonium ion group, amine group, a salt of an amine group, or the like are present in an amount of 1 to 100% and preferably 10 to 100% based on the total structural units of the polycation. If the proportion of the cationic structural units is too small, the complex formed by the interaction of the polycation and the water-insoluble polyanion tends to show a decrease in strength. On the contrary, if the proportion of the cationic structural units is too high, the method becomes uneconomical.

The polycation used in the present invention usually has a molecular weight in the range of 1,000 to 10,000,000. If the molecular weight is too low, the formed complex shows a descrease in strength. On the contrary, if the molecular weight is too high, the viscosity of the aqueous medium having the polycation dissolved or suspended therein is increased to impair the operating efficiency.

In the practice of the present invention, the polycation may be dissolved in water and used as an aqueous solution. If at least a part of the polycation is insoluble in water, it may be used as a suspension.

The aqueous medium used in the present invention may comprise water, an aqueous solution or an aqueous suspension according to the intended purpose. For example, a buffer solution, an aqueous solution of the substrate, a culture medium, and an aqueous solution of a water-soluble organic compound such as ethyl alcohol and the like can be used as the aqueous medium according to the need. Moreover, an aqueous suspension of an enzymatically active material insoluble in water or the like can also be used as the aqueous medium according to the need. It is not precluded that the aqueous medium further contains one or more substances which do not interfere with the practice of the present invention. Where a polycation falling under the above category I or II is added to the aqueous medium, no particular limitation is placed on the hydrogen ion concentration of the aqueous medium. However, where a polycation falling under the above category III or IV and containing a salt of an amine groups is added to the aqueous medium, it is preferable to use an acid pH lower than 7. Since the aqueous medium usually comes into contact with an enzymatically active material as described hereinbelow, it is necessary to select appropriate conditions (e.g., hydrogen ion concentration, the type of concentration of the solute and the suspensoid, and temperature) which do not deactivate the enzymatically active material. In the practice of the present invention, the concentration of the polycation in the aqueous medium is generally in the range of 0.01 to 70% by weight and preferably 0.1 to 50% by weight. If the concentration is too low, the yield of the immobilized preparation of enzymatically active material is reduced. On the contrary, if the concentration is too high, the viscosity of the aqueous medium is increased to make the method impractical.

The enzymatically active materials which can be used in the present invention include enzymes, microorganisms, cell fractions and the like. Among them, no particular limitation is placed on the type of enzyme used. Typical examples of useful enzymes are given in the following.

Oxidoreductases

Amino acid oxidases, uricase, catalase, xanthine oxidase, glucose oxidase, glucose-6-phosphate dehydrogenase, glutamate dehydrogenases, cytochrome c oxidase, tyrosinase, lactic dehydrogenase, peroxidases, 6-phosphogluconate dehydrogenase, malate dehydrogenase and the like.

Transferases

Aspartate acetyltransferase, aspartate aminotransferase, amino acid aminotransferases, glycine aminotransferase, glutamic-oxaloacetic aminitransferase, glutamic-pyruvic aminitransferase, creatine phosphokinase, histamine methyltransferase, pyruvate kinase, fructokinase, hexokinase, s-lysine acetyltransferase, leucine aminopeptidase and the like.

Hydrolases

Asparaginase, acetylcholinesterase, aminoacylase, arginase, L-arginine deiminase, invertase, urease, uricase, urokinase, esterases, kallikrein, chymotrypsin, trypsin, thrombin, naringinase, nucleotidases, papain, hyaluronidase, plasmin, pectinase, hesperidinase, pepsin, penicillinase, penicillin amidase, phospholipase, phosphatases, lactase, lipase, ribonucleases, rennin and the like.

Lyases

Aspartate decarboxylases, aspartase, citratelyase, glutamate decarboxylases, histidine ammonia-lyase, phenylalanine ammonia-lyase, fumarase, fumarate hydrase, malate synthetase and the like.

Isomerases

Alanine racemase, glucose isomerase, glucosephosphate isomerase, glutamate racemase, lactate racemase, methionine racemase and the like.

Ligases

Asparagine synthetase, glutathione synthetase, glutamine synthetase, puruvate synthetase and the like.

No particular limitation is placed on the type of microorganism used in the present invention, provided that it serves as a source of enzyme. The microorganisms which can be used in the present invention include, for example, bacteria, fungi, slime molds, lichens, algae, protozoa and other microorganisms that contain enzymes as enumerated above. These microorganisms may comprise either living cells or a preparation obtained by subjecting living cells to freeze-drying, freezing and thawing, acetone treatment, heat treatment or the like. The cell fractions which can be used in the present invention include microbial cell wall, mitochondria, microsomes, organelles, rami and soluble fraction that contain enzymes as enumerated above, as well as mixtures of the foregoing. The enzymatically active material used in the present invention may comprise either a single enzyme or a complex enzyme system. Moreover, two or more enzymatically active materials can be used in combination.

No particular limitation is placed on the type of water-insoluble polyanion used in the present invention, provided that it has any desired form suitable for the intended use of the resulting immobilized preparation of enzymatically active material and contains an anionic group which can react with the above-described polycation to form a strong complex. Although the water-insoluble polyanion can have any desired form suitable for the intended purpose, it is usually used in the form of a solid mass, a hydrogel, a suspension of a solid or liquid polymer, or the like. In order that the water-insoluble polyanion of the present invention may react with the above-described polycation to form a strong complex, it must contain an anionic group which can be, for example, a carboxylic acid group or a salt thereof, a sulfonic acid group or a salt thereof, a sulfuric ester group or a salt thereof, or a phosphoric ester group or a salt thereof. Specific examples of useful polyanions are given in the following.

(a) Polymers containing a carboxylic acid group or a salt thereof

Homopolymers, copolymers and graft polymers containing, as a monomer, a carboxylic acid (such as acrylic acid, methacrylic acid, maleic acid, fumaric acid, itaconic acid, etc.) or a salt thereof, as well as carboxyl-containing polysaccharides (such as alginic acid, pectin, carboxymethyl celulose, etc.) and salts thereof.

(b) Polymers containing a sulfonic acid group or a salt thereof

Homopolymers, copolymers and graft polymers containing, as a monomer, a sulfonic acid (such as 2-acrylamido-2-methylpropanesulfonic acid, 2-acrylamidoethanesulfonic acid, 2-methacrylamidoethanesulfonic acid, vinylsulfonic acid, allylsulfonic acid, styrenesulfonic acid, etc.) or a salt thereof.

(c) Polymers containing a sulfuric ester group or a salt thereof

Sulfuric ester compounds (such as carrageenan, furcellan, agar, ce-lulose sulfate, starch sulfate, sulfated starch, sulfated polyvinyl alcohol, etc.) and salts thereof.

(d) Polymers containing a phosphoric ester group or a salt thereof

Homopolymers, copolymers and graft polymers containing, as a monomer, a phosphoric ester (such as acid phosphoxyethyl methacrylate, acid phosphoxypropyl acrylate, acid phosphoxypropyl methacrylate, etc.) or a salt thereof, as well as phosphated polyvinyl alcohol, starch phosphate and salts thereof.

In the practice of the present invention, for example, a water-insoluble or water-insolubilized form of polymers as described above can be used as the water-insoluble polyanion of the present invention. For this purpose, such polymers may be used alone or in admixture. The term "water-insoluble polyanion" as used herein denotes water-insoluble polyanions obtained, for example, by crosslinking a polymer as described above according to conventional procedure so as to render them insoluble in water, water-insoluble polyanions obtained, in the practice of the present invention, by keeping a polymer as described above or an aqueous solution thereof at a temperature lower than its solidifying point, and the like.

In the above-described water-insoluble polyanion, the anionic functional group is generally present in an amount of 1 to 70% by weight and preferably 5 to 60% by weight.

As stated before, the water-insoluble polyanion of the present invention can be used in either solid or liquid form. Specific examples of water-insoluble polyanions in solid form include a hydrogel having a water content of, for example, not less than 100% by weight, a solid mass having a water content of less than 100% by weight, and the like. Water-insoluble polyanions in solid form can be prepared according to the method of crosslinking through ionic bonds (for example, by bringing a water-soluble salt of alginic acid into contact with an aqueous solution, such as an aqueous solution of calcium chloride, which can cause gelation of the salt) or the method of crosslinking through covalent bonds by means of radical reaction, condensation reaction or the like (for example, by mixing acrylic acid with a radical crosslinking agent and then subjecting the mixture to radical polymerization). It is to be understood that water-insoluble polyanions obtained by introducing an anionic group into crosslinked polymers (for example, water-soluble polyanions obtained by introducing the sulfonic acid group into crosslinked polymers prepared from styrenedivinylbenzene or phenol-formaldehyde) can also be used in the present invention. Further practicable methods for obtaining water-insoluble polyanions in solid form are, for example, to cool κ-carrageenan to a temperature lower than its solidifying point, to keep a polyethylene resin having the sulfonic acid group introduced thereinto at a temperature lower than its solidifying point, and the like.

Where a water-insoluble polyanion in solid form is used in the present invention, any desired shape can be given thereto according to the intended purpose. For example, a granular water-insoluble polyanion can be prepared by adding a water-soluble salt of alginic acid dropwise to a gelling solution therefor. Moreover, a sheet-like or filmy water-insoluble polyanion can be prepared by spreading a mixture of acrylic acid and a radical crosslinking agent on a shallow dish and then polymerizing the mixture. Thus, according to the intended purpose, the water-insoluble polyanion of the present invention can be shaped, for example, into sheets, films, granules, fibers, tubes, hollow fibers, nets and the like.

In the practice of the present invention, the water-insoluble polyanion can also be used in the form of a suspension. Such a suspension can be prepared, for example, by suspending a water-insoluble form of a solid or liquid polymer as described above in water or by dissolving or suspending it in a water-immiscible solvent and then suspending the resulting solution or suspension in water.

In immobilizing an enzymatically active material according to the method of the present invention, the enzymatically active material is brought into contact with a water-insoluble polyanion. Where the water-insoluble polyanion is used in solid form, the enzymatically active material can be brought into contact with the surfaces of the water-insoluble polyanion. Where the water-insoluble polyanion is present in the liquid phase, the enzymatically active material may be suspended in the liquid phase. Alternatively, a solution or suspension of the enzymatically active material in water or an aqueous solution may be brought into contact with the water-insoluble polyanion. Subsequently to this step, the water-insoluble polyanion in contact with the enzymatically active material is brought into contact with a polycation-containing aqueous medium to complete the immobilization procedure. In another embodiment, the immobilization procedure can be carried out in one step by dissolving or suspending the enzymatically active material in a polycation-containing aqueous medium and bringing the resulting solution or suspension into contact with the water-insoluble polyanion. It is to be understood that, during the above-described immobilization procedure, one or more substances which do not interfere with the practice of the present invention may be present in the enzymatically active material, the aqueous solution or suspension thereof and the polycation-containing aqueous medium.

No particular limitation is placed on the manner in which the enzymatically active material is brought into contact with the water-insoluble polyanion, provided that they can substantially contact each other. For example, the enzymatically active material may be sprinkled on the water-insoluble polyanion. In the embodiment in which a solution or suspension of the enzymatically active material in water or an aqueous solution and the polycation-containing aqueous medium are brought into contact with the water-insoluble polyanion, it is preferable to immerse or suspend the water-insoluble polyanion in the polycation-containing aqueous medium. In the above-described reaction, the water-insoluble polyanion and the polycation-containing aqueous medium are used in such a proportion that the ratio of the equivalents of the cationic group of the latter to the equivalents of the anionic group of the former is in the range of 0.01 to 100 and preferably in the range of 0.1 to 10. If the amount of the cationic group is too small, the gel does not harden to a full degree. On the contrary, if the amount of the cationic group is too large, the method becomes uneconomical.

The above-described contact reaction is carried out at a temperature in the range of $-20°$ to $100°$ C. and preferably in the range of $0°$ to $80°$ C. In the practice of the present invention, the pH of the water, aqueous solution or aqueous medium used to dissolve or suspend the enzymatically active material may vary widely, depending on the nature of the enzymatically active material. However, it is generally in the range of 1 to 12 and preferably in the range of 2 to 9.

According to the present method of immobilizing enzymatically active materials, the immobilized preparation of enzymatically active material resulting from the above-described reaction may further be brought into contact with an aqueous medium containing a polyanion and, if desired, the enzymatically active material, whereby a novel immobilized preparation of enzymatically active material is obtained. Specifically, an enzymatically active material can be immobilized in layers by using a polyanion-containing aqueous medium and a polycation-containing aqueous medium alternately.

The immobilized preparation of enzymatically active material obtained by the method of the present invention can be stably stored by washing it with a buffer solution, if necessary, and keeping it at a temperature ranging from $-20°$ C. to room temperature.

Since the immobilized preparation of enzymatically active material obtained by the method of the present invention is insoluble in water, the enzymatic reaction can be continuously carried out for a long period of time by packing it into a column and passing therethrough a solution of the substrate. Also by using it batchwise, the same enzymatic reaction can be carried out repeatedly. Moreover, since the method of the present invention allows the surface of an electrode to be coated with a film of an enzymatically active material and serves to immobilize an enzymatically active material on the outer or inner surface of a tubular body, its practical application in the fields of enzyme electrodes, medical analyzers and artificial organs is anticipated. Furthermore, the immobilized preparation of enzymatically active material obtained by the method of the present invention may be utilized in the field of fermentation to facilitate continuous and effective fermentation reaction. It is applicable to various types of fermentation. For example, where foaming is involved, it can be used in a fluidized-bed fermenter as well as a fixed-bed fermenter.

The present invention is further illustrated by the following examples. However, these examples are not to be construed to limit the scope of the invention.

EXAMPLE 1

A solution was prepared by dissolving 2 g of poly(vinylbenzyl-trimethylammonium chloride) in 100 ml of physiological saline. After this solution was sterilized by steam at $120°$ C. for 15 minutes, 50 loopfuls of J.B.A. (Japan Brewer's Association) No. 6 yeast was added thereto and suspended therein.

On the other hand, a solution was prepared by dissolving 10 g of sodium 2-acrylamido-2-methylpropanesulfonate and 1 g of N,N'-methylenebisacrylamide in 89 g of water, and nitrogen was bubbled therethrough at $5°$ C. for an hour. To this solution were added 1 ml of a 0.05% aqueous solution of ammonium persulfate and 0.04 ml of N,N,N',N'-tetramethylethylenediamine. After nitrogen was bubbled through the aqueous solution for 30 minutes, polymerization reaction was effected at $30°$ C. for 30 minutes and then $70°$ C. for an hour. Ten grams of the polymer obtained in the form of a hydrogel was cut into cubes of 3 mm size and then sterilized at $120°$ C. for 15 minutes.

Then, these hydrogel cubes were aseptically added to and immersed in the aforesaid yeast suspension in the poly(vinylbenzyltrimethylammonium chloride) solution, which was kept at $20°$ C. for an hour. At the end of this period, the yeast suspension was separated and the hydrogel cubes were washed twice with previously sterilized physiological saline. Thereafter, they were added to and immersed in 100 ml of a culture medium for yeast which had been sterilized at $120°$ C. This culture medium contained 10% of glucose, 0.15% of yeast extract, 0.25% of ammonium chloride, 0.1% of sodium chloride, 0.55% of dipotassium phosphate, 0.01% of magnesium sulfate, 0.001% of calcium chloride and 0.3% of citric acid. After its temperature was maintained at $30°$ C. for 40 hours, the culture medium had an ethanol concentration of 2.5%. Moreover, yeast colonies were observed in the vicinity of the surfaces of the hydrogel cubes.

EXAMPLE 2

A solution was prepared by dissolving 2 g of sodium alginate (manufactured and sold by Kamogawa Kasei Co. under the trade name of "Duck Algin NSPM") in 98 g of water. After being sterilized at $120°$ C. for 15 minutes, this solution was aseptically added dropwise to a 5% aqueous solution of calcium chloride which had been sterilized at $120°$ C. for 15 minutes, so that granular calcium alginate gel was obtained. This gel was aseptically packed into a jacketed glass column having a diameter of 2 cm and a height of 10 cm.

On the other hand, a nutrient medium containing 0.5% of glucose, 1.25% of yeast extract, 1.0% of peptone, 0.5% of meat extract and 0.5% of sodium chloride (pH 7.0) was inoculated with Serratia marcescens and then shaken at 30° C. for 16 hours. In 500 ml of the resulting culture medium having microbial cells suspended therein was dissolved 1.0 g of polyamine-sulfone (manufactured and sold by Toyobo Co. under the trade name of "PAS-H-40") which had previously been sterilized at 120° C. for 15 minutes.

This solution was passed through the aforesaid column from the bottom at a flow rate of 8 ml/hr, its internal temperature being kept at 30° C. After 24 hours, the passage of the solution was discontinued. On the other hand, 2% of "PAS-H-40" was dissolved in a fresh medium having the same composition as described above but containing no microbial cells. This solution was sterilized at 120° C. for 15 minutes and then passed through the column at a flow rate of 8 ml/hr, its internal temperature being kept at 30° C. After 60 hours, the effluent emerging from the outlet of the column had an isoleucine concentration of 2.3 mg/ml. Moreover, colonies were observed both in the vicinity of the surfaces of the gel and the interior of the gel.

EXAMPLES 3

A solution was prepared by dissolving 4 g of κ-carrageenan (manufactured and sold by Sansho Co. under the trade name of "Genugel-WG") in 96 g of water. After being sterilized at 120° C. for 15 minutes, this solution was kept at 50° C. and aseptically added dropwise to a 5% aqueous solution of calcium chrloride (at 20° C.) which had been sterilized at 120° C. for 15 minutes, so that granular calcium alginate gel was obtained. This gel was aseptically packed into a jacketed glass column having a diameter of 2 cm and a height of 10 cm.

On the other hand, a culture medium having Serratia marcescens suspended therein was prepared in the same manner as described in Example 2. In 500 ml of the resulting culture medium was dissolved 20 g of poly(4-vinyl-1-methylpyridinium chloride) which had previously been sterilized at 120° C. for 15 minutes.

This solution was passed through the aforesaid column from the bottom at a flow rate of 8 ml/hr, its internal temperature being kept at 30° C. After 24 hours, the passage of the solution was discontinued. On the other hand, 4% of poly(4-vinyl-1-methylpyridinium chloride) was dissolved in a fresh medium having the same composition as described in Example 2 but containing no microbial cells. This solution was sterilized at 120° C. for 15 minutes and then passed through the column at a flow rate of 8 ml/hr, its internal temperature being kept at 30° C. After 60 hours, the effluent emerging from the outlet of the column had an isoleucine concentration of 2.0 mg/ml. Thereafter, a fresh medium having the same composition as described in Example 2 but containing no polycation was passed through the column. After 60 hours, the effluent emerging from the outlet of the column had an isoleucine concentration of 2.5 mg/ml.

What is claimed is:

1. A method of immobilizing enzymatically active materials which comprises bringing an aqueous medium comprising a polycation and an enzymatically active material into contact with a water-insoluble polyanion, whereby the enzymatically active material is fixed as a film on the surface of the water-insoluble polyanion.

2. The method of claim 1 wherein the polycation comprises at least one polymer selected from polymers containing a quaternary ammonium ion group in the backbone, polymers containing a quaternary ammonium salt group in the side chains, polymers containing an amine group or a salt thereof in the backbone, or polymers containing an amine group or a salt thereof in the side chains.

3. The method of claim 1 wherein the enzymatically active material comprises a member selected from the group consisting of enzymes, microorganisms and cell fractions.

4. The method of claim 1 wherein the water-insoluble polyanion comprises at least one polymer selected from polymers containing a carboxylic acid group or a salt thereof, polymers containing a sulfonic acid group or a salt thereof, polymers containing a sulfuric ester group or a salt thereof, or polymers containing a phosphoric ester group or a salt thereof.

5. The method of claim 1 wherein the water-insoluble polyanion and the polycation-containing aqueous medium are used in such a proportion that the ratio of the equivalents of the cationic group to the equivalents of the anionic group is in the range of 0.01 to 100.

6. The method of claim 1 wherein the temperature at which the polycation-containing aqueous medium and the enzymatically active material are brought into contact with the water-insoluble polyanion is in the range of −20° to 100° C.

* * * * *